United States Patent
Liao

(10) Patent No.: US 10,980,464 B2
(45) Date of Patent: Apr. 20, 2021

(54) SYSTEM AND METHOD FOR MEASURING PHYSIOLOGICAL SIGNAL

(71) Applicant: Singular Wings Medical Co., Ltd., Hsinchu County (TW)

(72) Inventor: Chin-Chang Liao, Hsinchu County (TW)

(73) Assignee: Singular Wings Medical Co., Ltd., Hsinchu County (TW)

(*) Notice: Subject to any disclaimer, the term of this patent is extended or adjusted under 35 U.S.C. 154(b) by 644 days.

(21) Appl. No.: 15/794,002

(22) Filed: Oct. 26, 2017

(65) Prior Publication Data

US 2019/0046060 A1 Feb. 14, 2019

(30) Foreign Application Priority Data

Aug. 11, 2017 (TW) .................................. 106127285

(51) Int. Cl.
*A61B 5/25* (2021.01)
*A61B 5/00* (2006.01)
(Continued)

(52) U.S. Cl.
CPC .............. *A61B 5/25* (2021.01); *A61B 5/0004* (2013.01); *A61B 5/0205* (2013.01); *A61B 5/053* (2013.01);
(Continued)

(58) Field of Classification Search
CPC ... A61B 5/0408; A61B 5/0004; A61B 5/0205; A61B 5/053; A61B 5/0245; A61B 5/0492; A61B 5/113
(Continued)

(56) References Cited

U.S. PATENT DOCUMENTS 8,444,640 B2 * 5/2013 Demarais ............. A61N 1/0551
606/41
10,391,314 B2 * 8/2019 Hoffer ................... A61B 5/0205
(Continued)

FOREIGN PATENT DOCUMENTS

| TW | I296103 | 4/2008 |
| TW | I507171 | 11/2015 |
| TW | M513674 | 12/2015 |

OTHER PUBLICATIONS

"Office Action of Taiwan Counterpart Application", dated May 28, 2018, p. 1-p. 3.

*Primary Examiner* — Aaron F Roane
(74) *Attorney, Agent, or Firm* — JCIPRNET

(57) ABSTRACT

The present invention provides a system and a method for measuring physiological signal. The system includes a plurality of electrodes and a measurement apparatus. A plurality of first electrodes of the electrodes are attached on a first area of a subject. A plurality of second electrodes of the electrodes are attached on a second area of the subject. The measurement apparatus is coupled to the electrodes and performs testing on the first electrodes and the second electrodes to obtain a plurality of testing results. The measurement apparatus selects one of the first electrodes as a first measuring electrode and selects one of the second electrodes as a second measuring electrode according to the testing results. The measurement apparatus measures a physiological signal of the subject through the first measuring electrode and the second measuring electrode.

16 Claims, 7 Drawing Sheets

(51) Int. Cl.
*A61B 5/0205* (2006.01)
*A61B 5/053* (2021.01)
*A61B 5/113* (2006.01)
*A61B 5/0245* (2006.01)
*A61B 5/296* (2021.01)

(52) U.S. Cl.
CPC ............ *A61B 5/0245* (2013.01); *A61B 5/113* (2013.01); *A61B 5/296* (2021.01)

(58) Field of Classification Search
USPC ........................................................ 600/301
See application file for complete search history.

(56) References Cited

U.S. PATENT DOCUMENTS

| | | | | |
|---|---|---|---|---|
| 2010/0114202 A1* | 5/2010 | Donofrio | ............... | A61N 1/025 607/4 |
| 2013/0197386 A1* | 8/2013 | Cho | ....................... | A61B 5/085 600/533 |

* cited by examiner

SYSTEM AND METHOD FOR MEASURING PHYSIOLOGICAL SIGNAL

CROSS REFERENCE TO RELATED APPLICATION

This application claims the priority benefit of Taiwan application serial no. 106127285, filed on Aug. 11, 2017. The entirety of the above-mentioned patent application is hereby incorporated by reference herein and made a part of specification.

BACKGROUND OF THE INVENTION

Field of the Invention

The invention relates to a measuring system and a measuring method, and particularly to a system and a method for measuring physiological signal.

Description of Related Art

Generally speaking, in the process of measuring physiological signal, a plurality of electrodes may be attached on the surface of a subject's body to measure a physiological signal of the subject via the electrodes, wire and a measurement apparatus connected to the electrodes and the wire. However, when the subject moves, some of the electrodes attached on the surface of the subject's body may be loosened and contacted poorly with the surface of the body, which causes error in the physiological signal measured by the measurement apparatus or even causes that the physiological signal of the subject cannot be measured.

SUMMARY OF THE INVENTION

The invention provides a system and a method for measuring physiological signal. When electrodes for measuring physiological signal are not in good contact with body surface or detached from the body surface, the system for measuring physiological signal can still measure the correct physiological signal.

In the invention, the system for measuring physiological signal includes a plurality of electrodes and a measurement apparatus. The electrodes include a plurality of first electrodes and a plurality of second electrodes. The first electrodes are configured to attach on a first area of a subject, and the second electrodes are configured to attach on a second area of the subject. The measurement apparatus is coupled to the first electrodes and the second electrodes, and performs testing on the first electrodes and the second electrodes to obtain a plurality of testing results. According to the testing results, the measurement apparatus selects one of the first electrodes as a first measuring electrode and selects one of the second electrodes as a second measuring electrode. The measurement apparatus measures a physiological signal of the subject through the first measuring electrode and the second measuring electrode.

In the invention, the method for measuring physiological signal includes the following steps. A plurality of electrodes are divided into a plurality of first electrodes and a plurality of second electrodes. The first electrodes are attached on a first area of a subject, and the second electrodes are attached on a second area of the subject. A measurement apparatus performs the following steps: performing testing on the first electrodes and the second electrodes to obtain a plurality of testing results; selecting one of the first electrodes as a first measuring electrode according to the testing results and selecting one of the second electrodes as a second measuring electrode according to the testing results; and measuring a physiological signal of the subject through the first measuring electrode and the second measuring electrode.

Based on the above, the measurement apparatus is configured to perform testing on the plurality of first electrodes and the plurality of second electrodes. The measurement apparatus can determine an electrode state of each of the first electrodes and an electrode state of each of the second electrodes according to the testing results. Therefore, the measurement apparatus can select one suitable electrode from the first electrodes as the first measuring electrode and select one suitable electrode from the second electrodes as the second measuring electrode, and measure and obtain the physiological signal of the subject through a closed loop formed by the first measuring electrode, the subject and the second measuring electrode. During the measurement period, even if the first measuring electrode or the second measuring electrode are not in good contact with the subject or detached from the body surface of the subject due to certain reasons, the measurement apparatus can still search for a substitutional first measuring electrode and a substitutional second measuring electrode respectively from the first electrodes and the second electrodes according to the testing results. Then the measurement apparatus can measure and obtain the physiological signal of the subject through the closed loop formed by the substitutional first measuring electrode, the subject and the substitutional second measuring electrode.

In order to make the aforementioned features and advantages of the disclosure more comprehensible, embodiments accompanying figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF EMBODIMENTS

Figure 1:
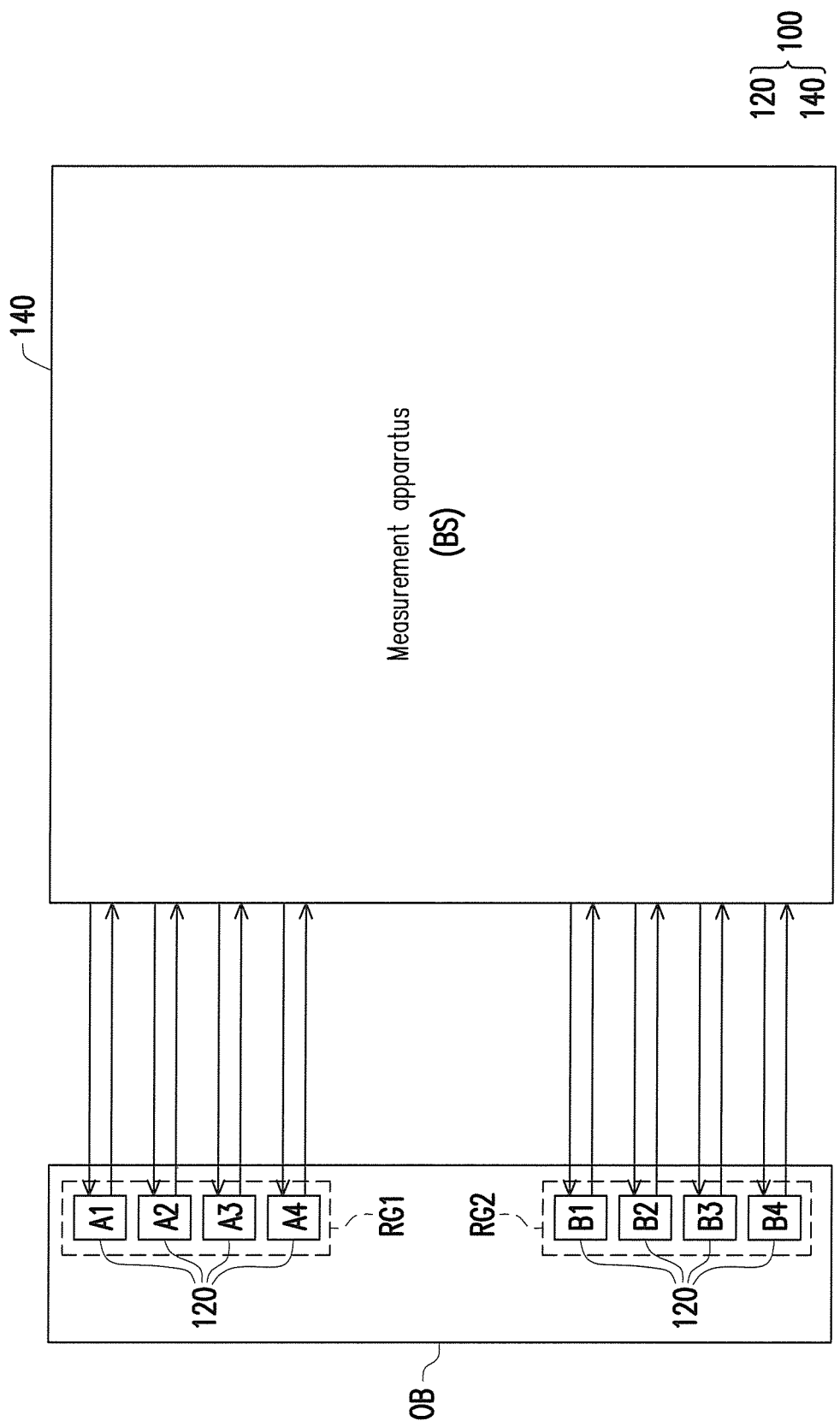
FIG. 1 is a block diagram illustrating a system for measuring physiological signal according to an embodiment of the invention.

Referring to FIG. 1, FIG. 1 is a block diagram illustrating a physiological signal measuring system 100 according to an embodiment of the invention. The physiological signal measuring system 100 may include a plurality of electrodes 120 and a measurement apparatus 140. The electrodes 120 may include a plurality of first electrodes and a plurality of second electrodes, wherein the number of the first electrodes may be the same as or different from the number of the second electrodes depending on actual application or requirement of design. For ease of description, in the following embodiments, the number of the first electrodes and the number of the second electrodes are set as four for exemplary purpose. The number of the first electrodes and the number of the second electrodes in other embodiments can be inferred based on the following descriptions. Therefore, as shown in FIG. 1, the electrodes 120 include four first electrodes A1-A4 and four second electrodes B1-B4, wherein the first electrodes A1-A4 are attached on a first area RG1 of a subject OB, and the second electrodes B1-B4 are attached on a second area RG2 of the subject OB.

The measuring apparatus 140 is coupled to the first electrodes A1-A4 and the second electrodes B1-B4. The measurement apparatus 140 may perform testing on the first electrodes A1-A4 and the second electrodes B1-B4 to obtain a plurality of testing results. The measurement apparatus 140 may select one of the first electrodes A1-A4 as a first measuring electrode according to the testing results and select one of the second electrodes B1-B4 as a second measuring electrode according to the testing results. Then the measurement apparatus 140 may measure and obtain a physiological signal BS of the subject OB through the first measuring electrode and the second measuring electrode. Thereafter, the measurement apparatus 140 may display the obtained physiological signal BS on a display to monitor the physiological state of the subject OB, or process and analyze the physiological signal BS, but the invention is not limited thereto. In an embodiment of the invention, the physiological signal BS may be, for example, a brainwave signal, an electrocardiogram signal or an electromyography signal and so on, which should not be construed as a limitation to the invention.

It can be understood that, by using the measurement apparatus 140 to perform testing on the first electrodes A1-A4 and the second electrodes B1-B4 continuously, the measurement apparatus 140 can determine an electrode state of each of the first electrodes A1-A4 and an electrode state of each of the second electrodes B1-B4 according to the testing results. Therefore, the measurement apparatus 140 may select one suitable electrode from the first electrodes A1-A4 as the first measuring electrode and select one suitable electrode from the second electrodes B1-B4 as the second measuring electrode. The measurement 140 may measure and obtain the physiological signal BS of the subject OB through a closed loop formed by the first measuring electrode, the subject OB and the second measuring electrode. In the measuring period, even if the first measuring electrode or the second measuring electrode is not in good contact with the subject OB or detached from the body surface of the subject OB due to certain reasons, the measurement apparatus 140 can still search for a substitutional first measuring electrode and a substitutional second measuring electrode respectively from the first electrodes A1-A4 and the second electrodes B1-B4 according to the testing results obtained by continuously performing testing on the first electrodes A1-A4 and the second electrodes B1-B4. Also, the measurement apparatus 140 can measure and obtain the physiological signal BS of the subject OB through the closed loop formed by the substitutional first measuring electrode, the subject OB and the substitutional second measuring electrode. In this manner, the measurement apparatus 140 can continuously obtain correct and continuing physiological signal BS so as to prevent the measurement from being interrupted or avoid measurement error. More details regarding the physiological signal measuring system of the invention are incorporated below.

Figure 2:
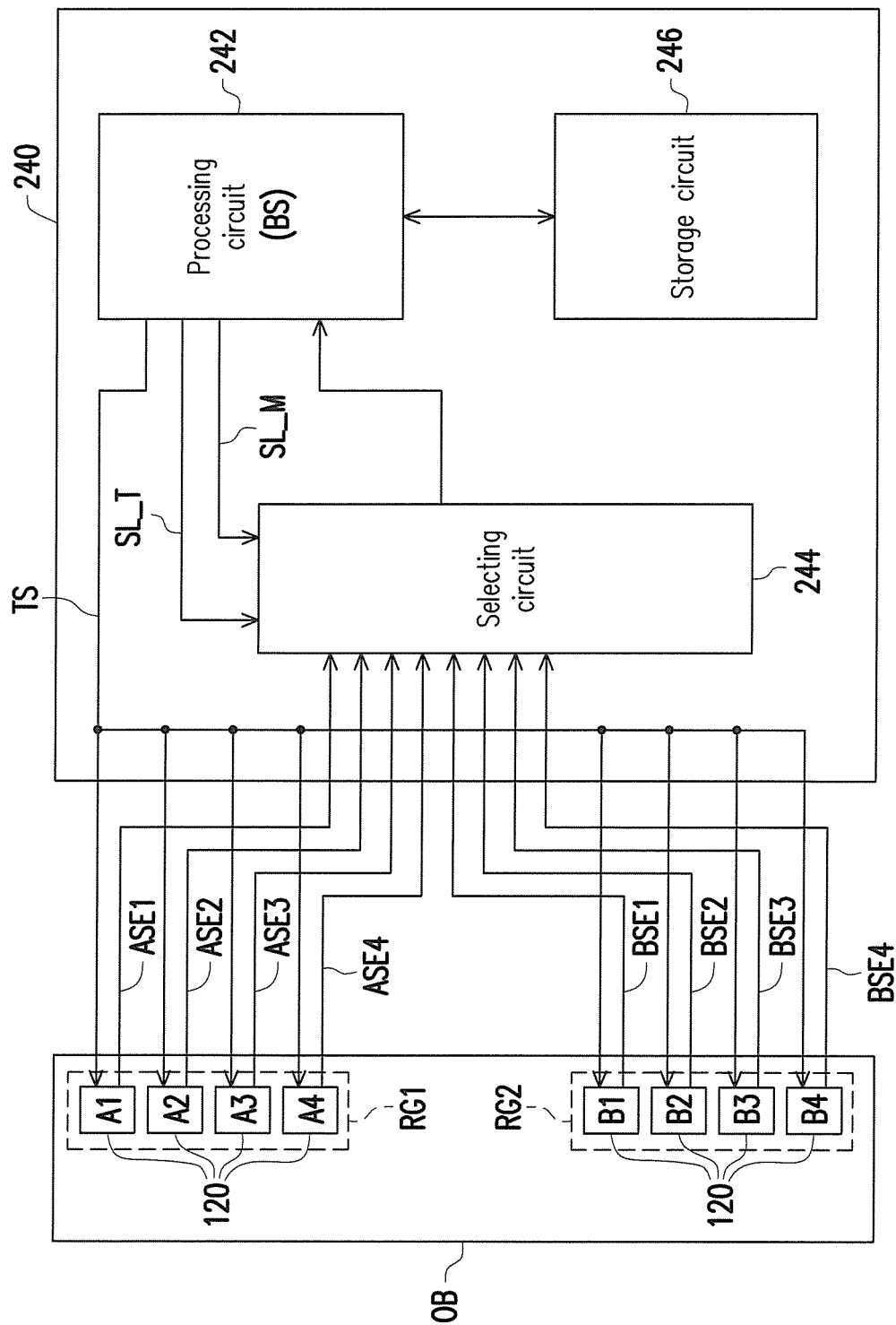
FIG. 2 is a schematic circuit block diagram illustrating a system for measuring physiological signal according to an embodiment of the invention.
Figure 3:
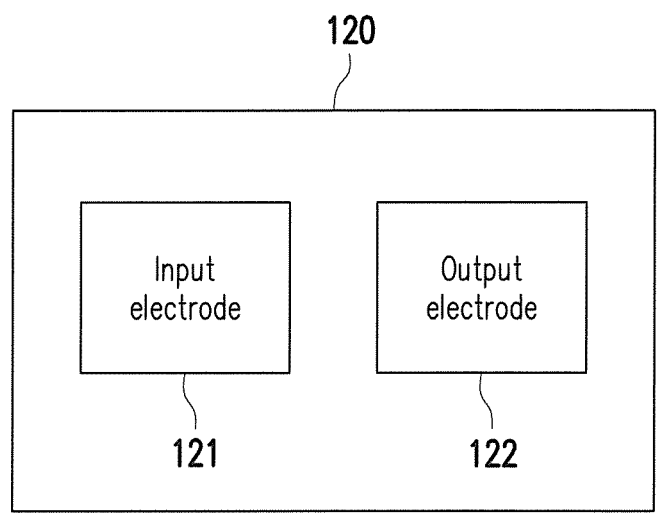
FIG. 3 is a schematic diagram illustrating a structure of an electrode according to an embodiment of the invention.

Referring to FIG. 2 and FIG. 3, FIG. 2 is schematic circuit block diagram illustrating a physiological signal measuring system 200 according to an embodiment of the invention, and FIG. 3 is a schematic diagram illustrating a structure of the electrodes 120 according to an embodiment of the invention, which may be applied to the physiological signal measuring system 200 of FIG. 2. The physiological signal measuring system 200 may include the plurality of electrodes 120 and a measurement apparatus 240. The electrodes 120 include four first electrodes A1-A4 and four second electrodes B1-B4, wherein the first electrodes A1-A4 are attached on the first area RG1 of the subject OB, and the second electrodes B1-B4 are attached on the second area RG2 of the subject OB. In addition, as shown in FIG. 3, each of the electrodes 120 may have an input electrode 121 and an output electrode 122, wherein the input electrode 121 and the output electrode 122 are separated from each other.

The measurement apparatus 240 is coupled to the electrodes 120. The measurement apparatus 240 can output a testing signal TS to the input electrode 121 of each of the electrodes 120. In an embodiment of the invention, the testing signal TS may be, for example, a voltage signal or a current signal. The measurement apparatus 240 may obtain, through the output electrode 122 of each of the electrodes 120, a varied testing signal that is the testing signal TS passing through the input electrode 121, the subject OB and the output electrode 122. The measurement apparatus 240 may use the varied testing signal as a corresponding testing result. For example, the measurement apparatus 240 may obtain, through the output electrode 122 of the first electrode A1, a varied testing signal that is the testing signal TS passing through the input electrode 121 of the first electrode A1, the subject OB and the output electrode 122 of the first electrode A1. Next, the varied testing signal can be served as a testing result ASE1. Therefore, the measurement apparatus 240 can obtain testing results ASE1-ASE4 respectively corresponding to the first electrodes A1-A4 and obtain testing results BSE1-BSE4 respectively corresponding to the second electrodes B1-B4. In particular, each of the testing results ASE1-ASE4 and BSE1-BSE4 may be the impedance value of each of the electrodes 120, for example.

In an embodiment of the invention, the measurement apparatus 240 may compare the impedance value of each of the first electrodes A1-A4 with the impedance value of each of the second electrodes B1-B4. Thereafter, the measurement apparatus 240 may select the first measuring electrode and the second measuring electrode respectively from the first electrodes A1-A4 and the second electrodes B1-B4, wherein the impedance value of the first measuring electrode and the impedance value of the second measuring electrode are best matched with each other. Furthermore, among the first electrodes A1-A4 and the second electrodes B1-B4, the difference between the impedance value of the selected first measuring electrode and the impedance value of the selected second measuring electrode is the smallest. Alternatively, the difference between the impedance value of the selected first measuring electrode and the impedance value of the selected measuring electrode is smaller than a predetermined value, wherein the predetermined value may be set depending on actual application or requirement of design. For example, if the measurement apparatus 240 determines that the impedance value of the first electrode A1 and the impedance value of the second electrode B2 are best matched with each other, the measurement apparatus 240 selects the first electrode A1 as the first measuring electrode and selects and the second electrode B2 as the second measuring electrode.

Based on that the impedance value of the first measuring electrode and the impedance value of the second measuring electrode are best matched with each other, the noise of the physiological signal BS obtained through the output electrode 122 of the first measuring electrode and the output electrode 122 of the second measuring electrode can be minimized.

In the embodiment of FIG. 2, the measurement apparatus 240 may include a processing circuit 242, a selecting circuit 244 and a storage circuit 246. The processing circuit 242 is coupled to the input electrode 121 of each of the electrodes 120. The processing circuit 242 can generate the testing signal TS and a testing selection signal SL_T, and output the testing signal TS to the input electrode 121 of each of the electrodes 120. The selecting circuit 244 is coupled to the output electrode 122 of each of the electrodes 120 to receive the testing results ASE1-ASE4 and BSE1-BSE4, and coupled to the processing circuit 242 to receive the testing selection signal SL_T. The selecting circuit 244 may transmit the testing results ASE1-ASE4 and BSE1-BSE4 to the processing circuit 242 in responding to the testing selection signal SL_T.

The storage circuit 246 is coupled to the processing circuit 242 and configured to store the testing results ASE1-ASE4 and BSE1-BSE4 of each of the electrodes 120. The processing circuit 242 may generate a measurement selection signal SL_M according to the testing results ASE1-ASE4 and BSE1-BSE4 of the electrodes 120. The selecting circuit 244 may select the first measuring electrode from the first electrodes A1-A4 and select the second measuring electrode from the second electrodes B1-B4 according to the measurement selection signal SL_M, and transmit the physiological signal BS from the first measuring electrode and the second measuring electrode to the processing circuit 242 for subsequent process.

Figure 4:
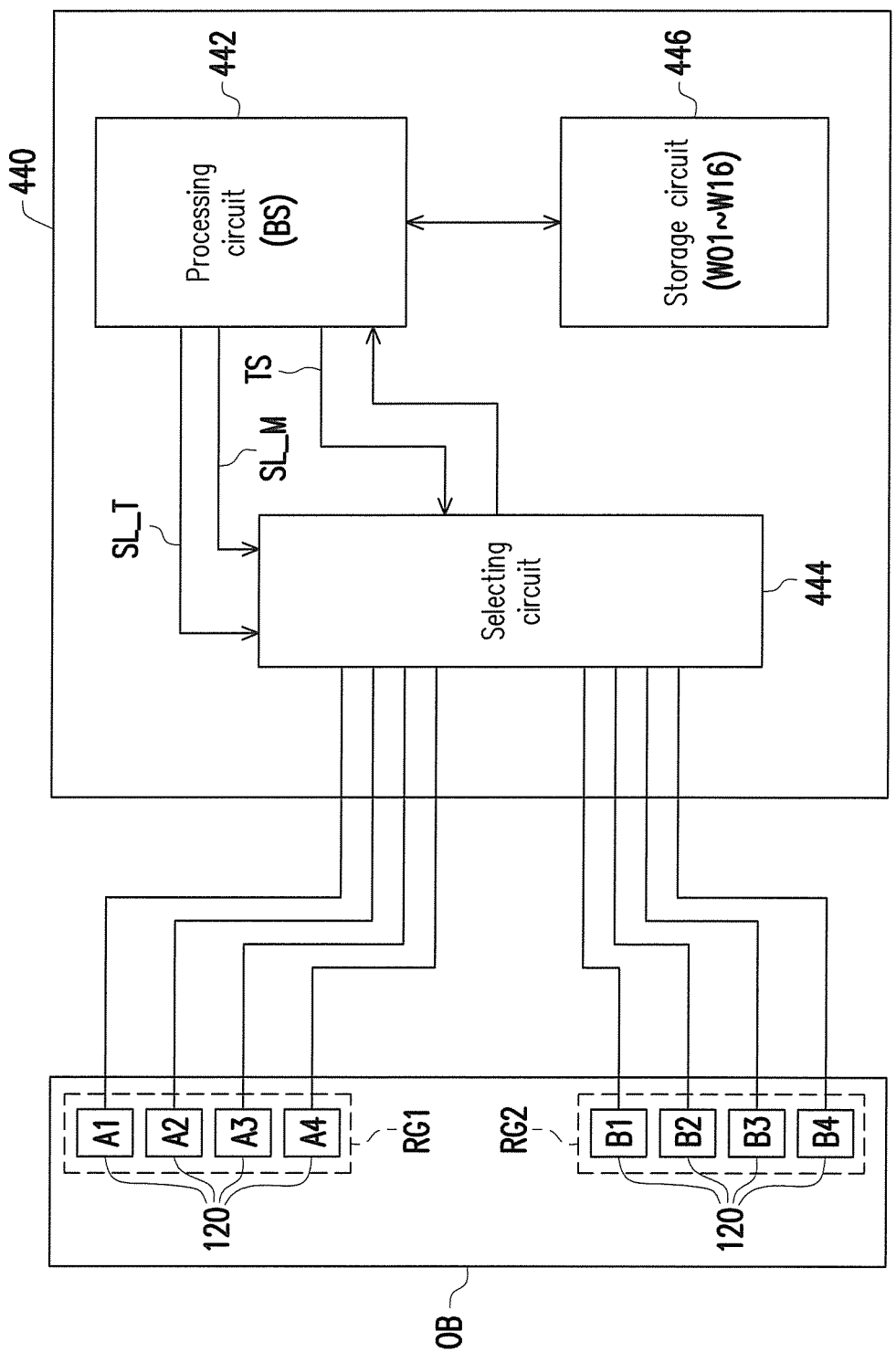
FIG. 4 is a schematic circuit block diagram illustrating a system for measuring physiological signal according to another embodiment of the invention.

Referring to FIG. 4, FIG. 4 is a schematic circuit block diagram of a physiological signal measuring system 400 according to another embodiment of the invention. The physiological signal measuring system 400 may include the plurality of electrodes 120 and a measurement apparatus 440. The electrodes 120 include the first electrodes A1-A4 and the second electrodes B1-B4, wherein the first electrodes A1-A4 are attached on the first area RG1 of the subject OB, and the second electrodes B1-B4 are attached on the second area RG2 of the subject OB.

The measurement apparatus 440 is coupled to the first electrodes A1-A4 and the second electrodes B4-B4. The measurement apparatus 440 may sequentially select one of the first electrodes A1-A4 as a first testing electrode, and sequentially select one of the second electrodes B1-B4 as a second testing electrode. The measurement apparatus 440 can output the testing signal TS to the first testing electrode and obtain a corresponding testing result from the second testing electrode. Alternatively, the measurement apparatus 440 may output the testing signal TS to the second testing electrode and obtain the corresponding testing result from the first testing electrode.

Specifically, the measurement apparatus 440 may select the first electrode A1 as the first testing electrode and select the second electrode B1 as the second testing electrode, and provide the testing signal TS to a loop formed by the first electrode A1 and the second electrode B1 to obtain a corresponding testing result W01. The measurement apparatus 440 may select the first electrode A1 as the first testing electrode and select the second electrode B2 as the second testing electrode, and provide the testing signal TS to a loop formed by the first electrode A1 and the second electrode B2 to obtain a corresponding testing result W02. The rest of selections can be inferred based on the above descriptions. Based on the sixteen loops formed by the four first electrodes A1-A4 and the four second electrodes B1-B4, the measurement apparatus 440 can obtain sixteen testing results W01-W16, wherein the testing results W01-W16 may be waveform signals, which should not be construed as a limitation to the invention.

The measurement apparatus 440 may compare the waveform of each of the testing results W01-W16 with the waveform of the testing signal TS to find the testing result of which the waveform is the least different from the waveform of the testing signal TS, and select the first measuring electrode and the second measuring electrode respectively from the first electrodes A1-A4 and the second electrodes B1-B4 accordingly. For example, if the measurement appeases 440 determines that difference between the waveform of the testing result W02 and the waveform of the testing signal TS is the least, then the measurement apparatus 440 selects the first electrode A1 as the first measuring electrode and selects the second electrode B2 as the second measuring electrode.

Based on that the difference between the waveform of the testing result generated by first measuring electrode and the second measuring electrode and the waveform of the testing result is the least, it represents that the signal has the least degree of attenuation when passing through the loop formed by the first measuring electrode and second measuring electrode. Therefore, the measurement apparatus 440 can obtain the physiological signal BS with the least degree of attenuation through the first measuring electrode and the second measuring electrode.

In the embodiment of FIG. 4, the merriment apparatus 440 may include a processing circuit 442, a selecting circuit 444 and a storage circuit 446. The processing circuit 442 generates the testing selection signal SL_T and the testing signal TS. The selecting circuit 444 is coupled to the processing circuit 442 to receive the testing selection signal SL_T and coupled to the electrodes 120. The selecting circuit 444 may select one of the first electrodes A1-A4 as the first testing electrode according to the testing selection signal SL_T and select one of the second electrodes B1-B4 as the second testing electrode according to the testing selection signal SL_T. The selecting circuit 444 may transmit the testing signal TS to one of the first testing electrode and the second testing electrode, receive a corresponding testing result from another of the first testing electrode and the second testing electrode, and transmit the corresponding testing result to the processing circuit 442. As described above, based on the sixteen loops formed by the four first electrodes A1-A4 and the four second electrodes B1-B4, the processing circuit 442 can obtain sixteen testing results W01-W16. The storage circuit 446 is coupled to the processing circuit 442 and configured to store the testing results W01-W16.

The processing circuit 442 compares the waveform of each of the testing results W01-W16 with the waveform of the testing signal TS to find the testing result of which the waveform is the least different from the waveform of the testing signal TS and generates the measurement selection signal SL_M accordingly. The selection circuit 444 selects the first measuring electrode and the second measuring electrode according to the measurement selection signal SL_M, and transmits the physiological signal BS of the subject OB from the first measuring electrode and the second measuring electrode to the processing circuit 442 for subsequent process.

In an embodiment of the invention, each of the measurement apparatuses 100, 200 and 400 may perform testing on the first electrodes A1-A4 and the second electrodes B1-B4 again at regular intervals to update the testing results, and select an updated first measuring electrode and an updated second measuring electrode respectively from the first electrodes A1-A4 and the second electrodes B1-B4 according to the updated testing results, so as to measure the physiological signal BS of the subject OB by using the updated first measuring electrode and the updated second measuring electrode.

In another embodiment of the invention, each of the measurement apparatuses 100, 200 and 400 may determine whether to perform testing on the first electrodes A1-A4 and the second electrodes B1-B4 again to update the testing results depending on whether the physiological signal BS is received. For example, when the measurement apparatuses 100, 200 and 400 cannot detect the physiological BS, the measurement apparatuses 100, 200 and 400 determine that the first measuring electrode and the second measuring electrode are abnormal. Then the measurement apparatuses 100, 200 and 400 can perform testing on the first electrodes A1-A4 and the second electrodes B1-B4 again to update the testing results, and select the updated first measuring electrode and the updated second measuring electrode respectively from the first electrodes A1-A4 and the second electrodes B1-B4 according to the updated testing results, so as to measure the physiological signal BS of the subject OB by using the updated first measuring electrode and the updated second measuring electrode.

In an embodiment of the invention, the processing circuits 242 and 442 of each of the above embodiments may be a hardware, a firmware or software that is stored in a memory and loaded and executed by a micro-controller, a microprocessor or a digital signal processor or a program code that can be executed by a machine. If the processing circuit is realized in the form of a hardware, then the processing circuit 242 and 442 may be achieved via a single integrated circuit chip, or can be achieved via a plurality of circuit chips, which should not be construed as a limitation to the invention. The plurality of circuit chips or a single integrated circuit chip may be realized via an application-specific integrated circuit (ASIC) or a field programmable gate array (FPGA). The above-mentioned memory may be, for example, a random access memory, a read-only memory or a flash memory and so on.

In an embodiment of the invention, the selecting circuit 244 of each of the above embodiments may be realized via a multiplexer or a demultiplexer, which should not be construed as a limitation to the invention. In an embodiment of the invention, the storage circuits 246 and 446 in each of the above embodiments may be realized via a memory circuit consisting of any form of memory such as a register, a static random access memory (SRAM), a dynamic random access memory (DRAM) or a flash memory and so on, which should not be construed as a limitation to the invention.

Figure 5:
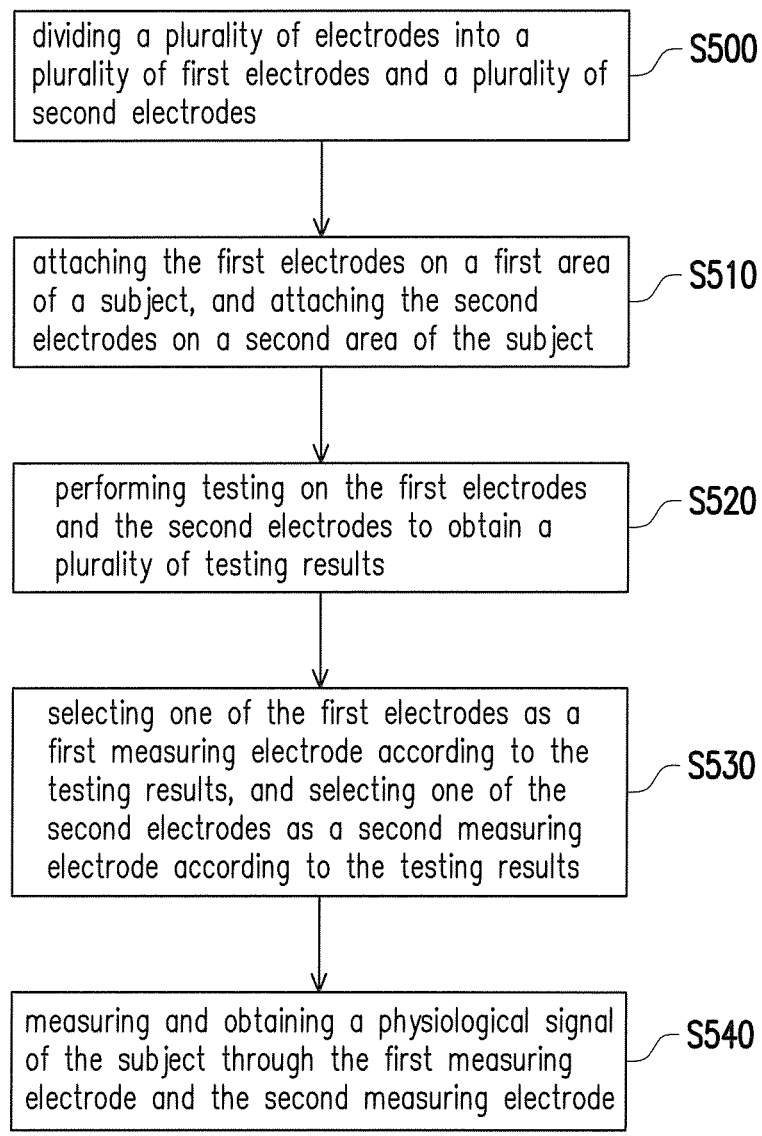
FIG. 5 is a flowchart illustrating steps of a method for measuring physiological signal according to an embodiment of the invention.

Referring to FIG. 1 and FIG. 5, FIG. 5 is a flowchart illustrating steps of a physiological signal measuring method according to an embodiment of the invention. First of all, in step S500, the electrodes 120 may be divided into first electrodes A1-A4 and second electrodes B1-B4. Next, in step S510, the first electrodes A1-A4 are attached on the first area RG1 of the subject OB, and the second electrodes B1-B4 are attached on the second area RG2 of the subject OB. Thereafter, in step S520, the measurement apparatus 140 may be used to perform testing on the first electrodes A1-A4 and the second electrodes B1-B4 to obtain a plurality of testing results. Subsequently, the measurement apparatus 140 selects one of the first electrodes A1-A4 as the first measuring electrode according to the testing results and selects one of the second electrodes B1-B4 as the second measuring electrode according to the testing results as shown in step 530. Lastly, the measurement apparatus 140 measures and obtains the physiological signal BS of the subject OB through the first measuring electrode and the second measuring electrode as shown in step S540.

Figure 6:
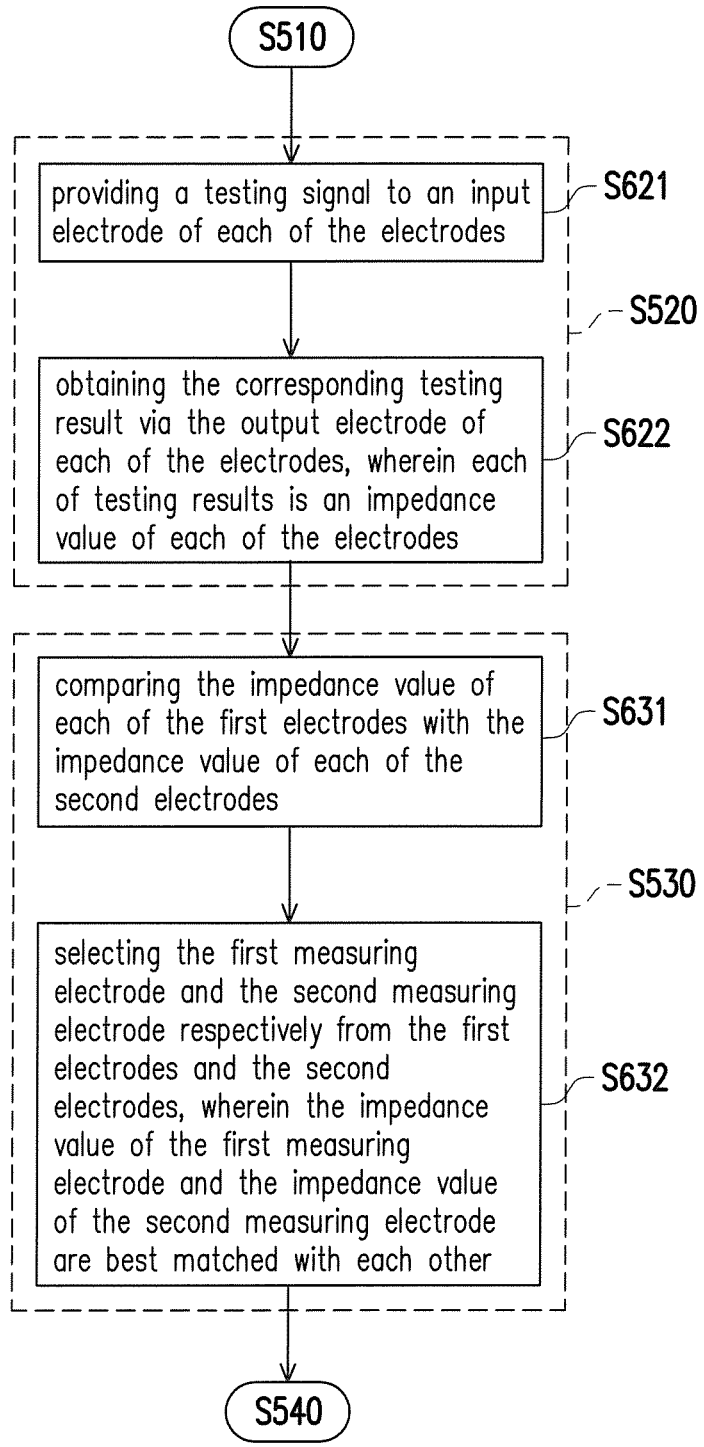
FIG. 6 is a flowchart illustrating details of step S520 and step S530 in FIG. 5 according to an embodiment of the invention.

Referring to FIG. 2, FIG. 3 and FIG. 6, FIG. 6 is a flowchart illustrating details of step S520 and step S530 in FIG. 5 according to an embodiment of the invention. The details of step S520 are described first. In step S621, the measurement apparatus 240 may be used to provide the testing signal TS to the input electrode of each of the electrodes 120. Thereafter, the output electrode 122 of each of the electrodes 120 may be used to obtain the corresponding test result (e.g., one of the testing results ASE1-ASE4 and BSE1-BSE4) as shown in step S622; each of the testing results ASE1-ASE4 and BSE1-BSE4 may be, for example, an impedance value of each of the electrodes 120.

The details of step S530 are described below. In step S631, the measurement apparatus 240 may be used to compare the impedance value of each of the first electrodes A1-A4 with the impedance value of each of the second electrodes B1-B4. Then, in step S632, the measurement apparatus 240 may be used to select the first measuring electrode and the second measuring electrode respectively from the first electrodes A1-A4 and the second electrodes B1-B4, wherein the impedance value of the first measuring electrode and the impedance value of the second measuring electrode are best matched with each other. Accordingly, the noise of the physiological signal BS obtained through the output electrode 122 of the first measuring electrode and the output electrode 122 of the second measuring electrode can be minimized.

Figure 7:
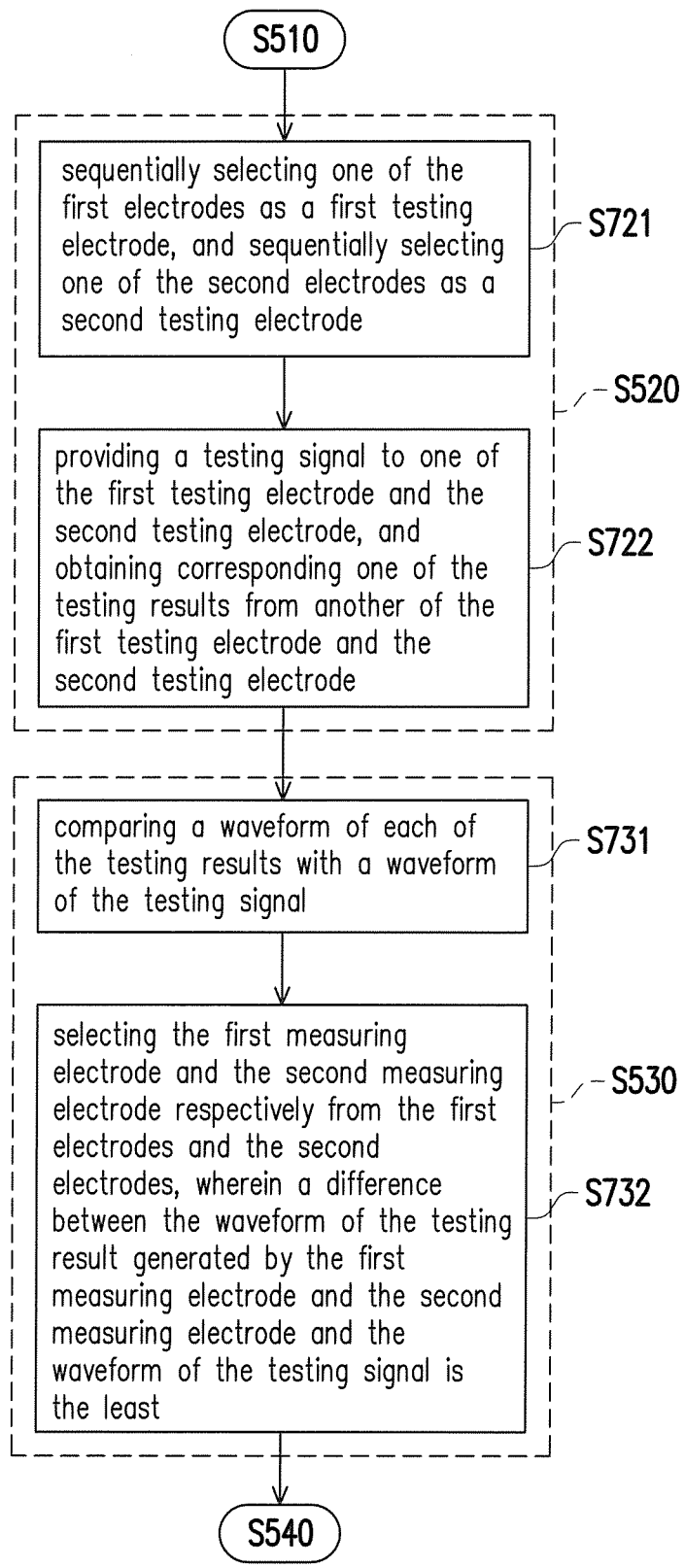
FIG. 7 is a flowchart illustrating details of step S520 and step S530 in FIG. 5 according to another embodiment of the invention.

Referring to FIG. 4 and FIG. 7, FIG. 7 is a flowchart of details of step S520 and S530 in FIG. 5 according to another embodiment of the invention. The details of step S520 are described first. In step S721, the measurement apparatus 440 may be used to sequentially select one of the first electrodes A1-A4 as the first testing electrode, and sequentially select one of the second electrodes B1-B4 as the second testing electrode. Subsequently, in step S722, the measurement apparatus 440 provides the testing signal TS to one of the first testing electrode and the second testing electrode, and obtains the corresponding testing result from another of the first testing electrode and the second testing electrode. Based on the sixteen loops formed by the four first electrodes A1-A4 and the four second electrodes B1-B4, the measurement apparatus 440 can obtain sixteen testing results W01-W16 by performing the step S721 and step S722.

Details of step S530 are described below. In step S731, the measurement apparatus 440 may be used to compare the waveform of each of the testing results W01-W16 with the waveform of the testing signal TS. Then, in step S732, the measurement apparatus 440 may be used to select the first measuring electrode and the second measuring electrode respectively from the first electrodes A1-A4 and the second electrodes B1-B4, wherein the difference between the waveform of the testing result generated by the first measuring electrode and the second measuring electrode and the waveform of the testing signal is the least.

Based on the above, in the system and method for measuring physiological signal provided by the invention, the measurement apparatus could perform testing on the plurality of first electrodes and the plurality of second electrodes. The measurement apparatus can determine the electrode state of each of the first electrodes and the electrode state of each of the second electrodes according to the testing results. Therefore, the measurement apparatus may select one suitable electrode from the first electrodes as the first measuring electrode, and select one suitable electrode from the second electrodes as the second measuring electrode. The measurement apparatus measures and obtains the physiological signal of the subject through the closed loop formed by the first measuring electrode, the subject and the second measuring electrode. During the measuring period, even if the first measuring electrode or the second measuring electrode is not in good contact with the subject or detached from the body surface of the subject due to certain reasons, the measurement apparatus can still search for the substitutional first measuring electrode and the substitutional second measuring electrode from the first electrodes and the second electrodes according to the testing results. Then the measurement apparatus can measure and obtain the physiological signal of the subject through the closed loop formed by the substitutional first measuring electrode, the subject and the substitutional second measuring electrode.

Although the invention has been disclosed by the above embodiments, the embodiments are not intended to limit the invention. It will be apparent to those skilled in the art that various modifications and variations can be made to the structure of the invention without departing from the scope or spirit of the invention. Therefore, the protecting range of the invention falls in the appended claims.

What is claimed is:

1. A system for measuring physiological signal, comprising:
 a plurality of electrodes, comprising a plurality of first electrodes and a plurality of second electrodes, wherein the first electrodes are configured to attach on a first area on a subject, and the second electrodes are configured to attach on a second area of the subject; and
 a measurement apparatus, coupled to the first electrodes and the second electrode, performing testing on the first electrodes and the second electrodes to obtain a plurality of testing results, selecting one of the first electrodes as a first measuring electrode according to the testing results, selecting one of the second electrodes as a second measuring electrode according to the testing results, and measuring a physiological signal of the subject through the first measuring electrode and the second measuring electrode.

2. The system for measuring physiological signal according to claim 1, wherein each of the electrodes comprises an input electrode and an output electrode, wherein:
 the measurement apparatus outputs a testing signal to the input electrode of each of the electrodes, and obtains a varied testing signal through the output electrode of each of the electrodes to serve as corresponding one of the testing results, wherein the varied testing signal that is the testing signal passing through the input electrode, the subject and the output electrode.

3. The system for measuring physiological signal according to claim 2, wherein:
 each of the testing results comprises an impedance value of each of the electrodes,
 wherein the measurement apparatus compares the impedance value of each of the first electrodes with the impedance value of each of the second electrodes, and selects the first measuring electrode and the second measuring electrode respectively from the first electrodes and the second electrodes, wherein the impedance value of the first measuring electrode and the impedance value of the second measuring electrode are best matched with each other.

4. The system for measuring physiological signal according to claim 2, wherein the measurement apparatus comprises:
 a processing circuit, coupled to the input electrode of each of the electrodes, and configured to generate the testing signal and a testing selection signal and output the testing signal to the input electrode of each of the electrodes;
 a selecting circuit, coupled to the output electrode of each of the electrodes to receive the testing result corresponding to the testing signal, and coupled to the processing circuit to receive the testing selection signal, wherein the selecting circuit transmits the testing result to the processing circuit in responding to the testing selection signal; and
 a storage circuit, coupled to the processing circuit and configured to store the testing results,
 wherein the processing circuit generates a measurement selection signal according to the testing results, the selecting circuit selects the first measuring electrode and the second measuring electrode according to the measurement selection signal, and transmits the physiological signal of the subject from the first measuring electrode and the second measuring electrode to the processing circuit.

5. The system for measuring physiological signal according to claim 1, wherein:
 the measurement apparatus sequentially selects one of the first electrodes as a first testing electrode, the measurement apparatus sequentially selects one of the second electrodes as a second testing electrode, the measurement apparatus outputs a testing signal to one of the first testing electrode and the second testing electrode, and obtains corresponding one of the testing results from another of the first testing electrode and the second testing electrode.

6. The system for measuring physiological signal according to claim 5, wherein:
 the measurement apparatus compares a waveform of each of the testing results with a waveform of the testing signal so as to select the first measuring electrode and the second measuring electrode respectively from the first electrodes and the second electrodes, wherein a difference between the waveform of the testing result generated by the testing signal passing through the first measuring electrode and the second measuring electrode and the waveform of the testing signal is least.

7. The system for measuring physiological signal according to claim 5, wherein the measurement apparatus comprises:
 a processing circuit, configured to generate a testing selection signal and the testing signal;
 a selecting circuit, coupled to the processing circuit to receive the testing selection signal, and coupled to the electrodes, wherein the selecting circuit transmits the testing signal to one of the first testing electrode and the second testing electrode in responding to the testing selection signal, receives the corresponding testing result from another of the first testing electrode and the second testing electrode, and transmits the corresponding testing result to the processing circuit; and a storage circuit, coupled to the processing circuit and configured to store the testing result, wherein the processing circuit generates a measurement selection signal according to the testing results, the selecting circuit selects the first measuring electrode and the second measuring electrode according to the measurement selection signal, and the selecting circuit transmits the physiological signal of the subject from the first measuring electrode and the second measuring electrode to the processing circuit.

8. The system for measuring physiological signal according to claim 1, wherein the measurement apparatus performs testing on the first electrodes and the second electrodes again at regular intervals to update the testing results, and selects the first measuring electrode and the second measuring electrode respectively from the first electrodes and the second electrodes according to the updated testing results.

9. The system for measuring physiological signal according to claim 1, wherein the measurement apparatus detects whether the physiological signal is abnormal, if it is determined that the physiological signal is abnormal, the measurement apparatus performs testing on the first electrodes and the second electrodes again to update the testing results, and select the first measuring electrode and the second measuring electrode respectively from the first electrodes and the second electrodes according to the updated testing results.

10. A method for measuring physiological signal, comprising:

dividing a plurality of electrodes into a plurality of first electrodes and a plurality of second electrodes;

attaching the first electrodes on a first area of a subject, and attaching the second electrodes on a second area of the subject; and performing the following steps by a measurement apparatus:

performing testing on the first electrodes and the second electrodes to obtain a plurality of testing results;

selecting one of the first electrodes as a first measuring electrode according to the testing results, and selecting one of the second electrodes as a second measuring electrode according to the testing results; and measuring a physiological signal of the subject through the first measuring electrode and the second measuring electrode.

11. The method for measuring physiological signal according to claim 10, wherein the step of performing testing on the first electrodes and the second electrodes to obtain the testing results comprises:

providing, by the measurement apparatus, a testing signal to an input electrode of each of the electrodes; and outputting, by an output electrode of each of the electrodes, a varied testing signal to the measurement apparatus to serve as corresponding one of the testing results, wherein the varied testing signal that is the testing signal passing through the input electrode, the subject and the output electrode.

12. The method for measuring physiological signal according to claim 11, wherein each of the testing results comprises an impedance value of each of the electrodes, wherein the step of selecting one of the first electrodes as the first measuring electrode according to the testing results and selecting one of the second electrodes as the second measuring electrode according to the testing results comprises:

comparing the impedance value of each of the first electrodes with the impedance value of each of the second electrodes; and selecting the first measuring electrode and the second measuring electrode respectively from the first electrodes and the second electrodes, wherein the impedance value of the first measuring electrode and the impedance value of the second measuring electrode are best matched with each other.

13. The method for measuring physiological signal according to claim 10, wherein the step of performing testing on the first electrodes and the second electrodes to obtain the testing results comprises:

sequentially selecting one of the first electrodes as a first testing electrode, and sequentially selecting one of the second electrodes as a second testing electrode; and providing a testing signal to one of the first testing electrode and the second testing electrode, and obtaining corresponding one of the testing results from another of the first testing electrode and the second testing electrode.

14. The method for measuring physiological signal according to claim 13, wherein the step of selecting one of the first electrodes as the first measuring electrode according to the testing results and selecting one of the second electrodes as the second measuring electrode according to the testing results comprises:

comparing a waveform of each of the testing results with a waveform of the testing signal, wherein a difference between the waveform of the testing result generated by the testing signal passing through the first measuring electrode and the second measuring electrode and the waveform of the testing signal is least.

15. The method for measuring physiological signal according to claim 10, further comprising:

performing testing on the first electrodes and the second electrodes again at regular intervals to update the testing results; and selecting the first measuring electrode and the second measuring electrode respectively from the first electrodes and the second electrodes according to the updated testing results.

16. The method for measuring physiological signal according to claim 10, further comprising:

detecting whether the physiological signal is abnormal;

if it is determined that the physiological signal is abnormal, performing testing on the first electrodes and the second electrodes again to update the testing results; and selecting the first measuring electrode and the second measuring electrode respectively from the first electrodes and the second electrodes according to the updated testing results.

\* \* \* \* \*